United States Patent
Kamida et al.

(10) Patent No.: US 8,294,317 B2
(45) Date of Patent: Oct. 23, 2012

(54) UNIDIRECTIONALLY-ENERGIZED BRUSHLESS DC MOTOR INCLUDING AC VOLTAGE OUTPUT WINDING AND MOTOR SYSTEM

(75) Inventors: Yoshihide Kamida, Ohtsu (JP); Yasuhiro Komatsu, Kyoto (JP)

(73) Assignees: Yoshihide Kamida (JP); Yasuhiro Komatsu (JP); Takeshi Isa (JP); Takeshi Yamaoka (JP)

( * ) Notice: Subject to any disclaimer, the term of this patent is extended or adjusted under 35 U.S.C. 154(b) by 353 days.

(21) Appl. No.: 12/742,057

(22) PCT Filed: Nov. 9, 2007

(86) PCT No.: PCT/JP2007/071826
§ 371 (c)(1),
(2), (4) Date: May 7, 2010

(87) PCT Pub. No.: WO2009/060544
PCT Pub. Date: May 14, 2009

(65) Prior Publication Data
US 2010/0277023 A1    Nov. 4, 2010

(51) Int. Cl.
*H02K 21/12* (2006.01)
(52) U.S. Cl. ......... 310/156.01; 310/156.53; 310/156.56; 310/268; 310/102 R; 415/916
(58) Field of Classification Search ............. 310/102 R, 310/156.01, 156.53, 156.56, 268; 415/916; H02K 21/12
See application file for complete search history.

(56) References Cited

U.S. PATENT DOCUMENTS

| 4,751,486 | A  | * | 6/1988 | Minato | 335/272 |
| 6,777,838 | B2 | * | 8/2004 | Miekka et al. | 310/67 R |
| 2004/0119366 | A1 | * | 6/2004 | Hosaka | 310/216 |
| 2010/0277023 | A1 | * | 11/2010 | Kamida et al. | 310/156.01 |

OTHER PUBLICATIONS

John K. Kim, "Novel Scheme of Driving Single Phase PM AC Motor in Uni-Direction", IEEE 2007.*

* cited by examiner

*Primary Examiner* — John K Kim
(74) *Attorney, Agent, or Firm* — Thomas, Kayden, Horstemeyer & Risley, LLP.

(57) ABSTRACT

A unidirectionally-energized brushless DC motor includes a disk attached to a frame, a plurality of plate-like permanent magnets disposed on the disk at equal intervals around the disk, magnetic cores fixed to the frame according to the plurality of permanent magnets, windings each of which is wound around the magnetic core and to which DC power is supplied, a predetermined number of magnetic cores fixed to the frame, and windings each of which is wound around the magnetic core and connected to a power consumption device. The permanent magnets are located such that an angle formed by a straight line passing through the center of the disk and the center of the permanent magnet and a normal line in the center of a magnetic pole plane of the permanent magnet ranges from 0° to 60°.

7 Claims, 8 Drawing Sheets

UNIDIRECTIONALLY-ENERGIZED BRUSHLESS DC MOTOR INCLUDING AC VOLTAGE OUTPUT WINDING AND MOTOR SYSTEM

CROSS REFERENCE TO RELATED APPLICATION

This application is the 35 U.S.C. §371 national stage of PCT application PCT/JP2007/071826, filed Nov. 9, 2007, the disclosure of which is hereby incorporated by reference.

TECHNICAL FIELD

The present invention relates to a unidirectionally-energized brushless DC motor including an AC voltage output winding and a motor system, particularly to a unidirectionally-energized brushless DC motor including an AC voltage output winding, the brushless DC motor rotating a rotating body to act as a motor and directly generating electric power by the rotation of the rotating body, and a motor system including the brushless DC motor.

BACKGROUND ART

Conventionally a motor and a power generator are mechanically coupled when electric power is generated by rotating the motor. Originally the motor and the power generator have the same structure, those are called the motor when a rotating body is rotated to obtain a driving force by supplying the electric power, and those are called the power generator when the rotating body is rotated by the driving force to generate an electromotive force in a winding. Therefore, a trial in which the power generation is performed by the rotation of the rotating body while the motor function is exerted by rotating the rotating body, that is, the trial in which the motor function and the power generator function are simultaneously exerted using the same rotating body has been made. As a result of the trial, for example, Patent Document 1 discloses a magnetic rotation motor power generator.

In the magnetic rotation motor power generator of Patent Document 1, the motor function and the power generator function are exerted by an electromagnet and the rotating body in which a permanent magnet is provided. More specifically, a rotating mode is realized when the permanent magnet of the rotating body comes close to the electromagnet, the rotating body is rotated by action and reaction of a magnetic force between the permanent magnet and the electromagnet, a power generation mode is realized until the permanent magnet comes close to the adjacent electromagnet since the permanent magnet passes by the electromagnet, and the permanent magnet changes a magnetic field around a winding of the electromagnet, whereby an electromotive force is generated by electromagnetic induction.

Patent Document 1: Japanese Unexamined Patent Publication No. 2005-245079

However, in the magnetic rotation motor power generator of Patent Document 1, the one electromagnet switches between the rotating mode and the power generation mode to realize the motor function and the power generator function in a time-division fashion. Accordingly, in the magnetic rotation motor power generator, unfortunately the electromotive force cannot continuously be obtained.

In view of the foregoing, an object of the present invention is to provide a unidirectionally-energized brushless DC motor including an AC voltage output winding, the brushless DC motor being able to exert the power generation function of being able to obtain the continuous electromotive force using the same rotating body, and a motor system including the brushless DC motor.

SUMMARY

To achieve the above object, a unidirectionally-energized brushless DC motor including an AC voltage output winding includes: a frame; a disk that is rotatably attached to the frame; a plurality of plate-like permanent magnets that are disposed on the disk at equal intervals around the disk, magnetic poles being formed in a surface and a back side of the permanent magnet; a predetermined number of first magnetic cores that are fixed to the frame according to the plurality of permanent magnets; a first winding that is wound around each of the first magnetic cores, DC power being supplied to the first winding; a predetermined number of second magnetic cores that are fixed to the frame; and a second winding that is wound around the second magnetic core and connected to a power consumption device, wherein the permanent magnet is located such that an angle formed by a straight line passing through a center of the disk and a center of the permanent magnet and a normal line in a center of a magnetic pole plane of the permanent magnet ranges from 0° to 60°, whereby, when constant DC current is continuously supplied to the first winding, a large-value narrow-angle torque in which a rotation angle range where the disk is rotated in a reverse direction is narrowed while a torque value is large and a small-value wide-angle torque in which a rotation angle range where the disk is rotated in a normal direction is spread while the torque value is small are generated in a characteristic curve of a rotation angle of the permanent magnet and an electromagnetic torque, the rotation angle of the permanent magnet being measured with respect to the permanent magnet in a stable equilibrium operating state based on the first magnetic core, a detent torque becoming zero in the stable equilibrium operating state, the detent torque being generated by an attractive force between the first magnetic core and the permanent magnet during non-power feeding to the first winding, the electromagnetic torque being generated by current of the first winding and the permanent magnet, and the power feeding is performed to the first winding only when the large-value narrow-angle torque is generated, or only when the small-value wide-angle torque is generated.

A unidirectionally-energized brushless DC motor including an AC voltage output winding provides the unidirectionally-energized brushless DC motor including an AC voltage output winding including the two disks that are coaxially fixed to each other, wherein a polarity of the permanent magnet disposed in one of the disks and a polarity of the permanent magnet disposed in the other disk are different from each other, and the first magnetic core is fixed such that one of end portions corresponds to the permanent magnet disposed in one of the disks while the other end portion corresponds to the permanent magnet disposed in the other disk.

A unidirectionally-energized brushless DC motor including an AC voltage output winding provides the unidirectionally-energized brushless DC motor including an AC voltage output winding wherein the even-numbered first magnetic cores exist, the first magnetic cores are fixed in a certain position of the disk and a position that is separated from the position by 180°, and identical current is passed through the two first windings that are wound around the first magnetic cores, the first windings being opposite each other, and the even-numbered second magnetic cores exist, the second magnetic cores are fixed in a certain position of the disk and a position that is separated from the position by 180°, and identical current is passed through the two second windings that are wound around the second magnetic cores, the second windings being opposite each other.

A unidirectionally-energized brushless DC motor including an AC voltage output winding provides the unidirectionally-energized brushless DC motor including an AC voltage output winding, wherein the frame and the disk are made of a non-metallic material.

A unidirectionally-energized brushless DC motor including an AC voltage output winding provides the unidirectionally-energized brushless DC motor including an AC voltage output winding, wherein, when the disk is stopped in the stable equilibrium state having the detent torque of zero because electric power is not supplied to the first winding, the second magnetic core is located with respect to the permanent magnet such that a positional relationship between the first winding and the permanent magnet becomes a positional relationship in which the torque in the normal direction of the disk or the torque in the reverse direction of the disk is continuously generated at a predetermined rotation angle of the disk when the supply of the electric power to the first winding is started.

To achieve the above object, a motor system includes: a unidirectionally-energized brushless DC motor including an AC voltage output winding; and a feeding mechanism that supplies electric power of a DC power supply to the first winding at the time a torque is obtained in the normal direction of the unidirectionally-energized brushless DC motor including the AC voltage output winding, temporarily rotates the disk in the reverse direction in starting up the unidirectionally-energized brushless DC motor including the AC voltage output winding, and supplies the electric power of the DC power supply to the first winding such that the permanent magnet located in a reverse rotation region where the torque is generated in the reverse direction during the stopping is moved to a normal rotation region where the torque is generated in the normal direction and such that the disk is turned to the normal rotation while the permanent magnet does not reach the reverse rotation region in the reverse rotation direction.

A motor system provides the motor system, wherein the unidirectionally-energized brushless DC motor including an AC voltage output winding further includes: a position detecting disk that is rotated in coaxial with the disk, a marker for determining a feeding region or a non-feeding region being disposed according to a rotation angle of the disk in the position detecting disk; and a sensor that detects the marker disposed in the position detecting disk, and the feeding mechanism includes a switch that switches whether power feeding is performed to the first winding according to the marker detection result of the sensor.

According to an embodiment, the unidirectionally-energized brushless DC motor includes: the electromagnet that includes the first magnetic core and the first winding to rotate the disk so as to correspond to the permanent magnet provided on the disk; and the electromagnet that includes the second magnetic core and the second winding to generate the electromotive force by the change in magnetic field of the permanent magnet provided in the rotating disk. Accordingly, the motor function of being able supply the electric power to the first winding to obtain the predetermined torque and the power generation function of being able to continuously obtain the electromotive force in the second winding can simultaneously be exerted using the disk that is of the same rotating body.

The large-value narrow-angle torque in which the electromagnetic torque has the large value and the small-value wide-angle torque in which the generated rotation angle has the large width are generated. Accordingly, the large torque is obtained with the small electric power when the electric power is supplied to the first winding at the time the large-value narrow-angle torque is generated. The feeding time can be lengthened when the electric power is supplied to the first winding at the time the small-value wide-angle torque is generated. Therefore, the current passed through the first winding can be increased, even if the time necessary to the increase and decrease in current passed through the first winding is lengthened due to self-inductance of the electromagnet including the first magnetic core and the first winding.

According to another embodiment, the unidirectionally-energized brushless DC motor includes the two disks, the polarity of the permanent magnet disposed in one of the disks and the polarity of the permanent magnet disposed in the other disk are different from each other, and the first magnetic core is fixed such that one of end portions corresponds to the permanent magnet disposed in one of the disks while the other end portion corresponds to the permanent magnet disposed in the other disk. Accordingly, because both the electromagnetic forces generated in the two end portions of the first magnetic core can be utilized to rotate the disk, the electric power-mechanical power energy conversion efficiency can be enhanced.

According to another embodiment, the first magnetic cores are fixed in a certain position of the disk and a position that is separated from the position by 180° so as to be opposite each other, and the second magnetic cores are fixed in a certain position of the disk and a position that is separated from the position by 180° so as to be opposite each other, and the identical current is passed through the two windings that are opposite each other. Therefore, the electromagnetic force in the radial direction is cancelled, so that a vibration can be decreased to reduce a noise.

According to another embodiment, the frame and the disk are made of the non-metallic material, so that an iron loss can be reduced.

According to another embodiment, when the disk is stopped because the electric power is not supplied to the first winding, the second magnetic core is located with respect to the permanent magnet such that the positional relationship between the first winding and the permanent magnet becomes the positional relationship in which the torque in the normal direction of the disk or the torque in the reverse direction of the disk is continuously generated at the predetermined rotation angle of the disk when the supply of the electric power to the first winding is started. Accordingly, when the power feeding to the first winding is started in the stable equilibrium state in which the disk is stopped, the disk can immediately be rotated in the normal direction or the reverse direction.

According to another embodiment, the motor system includes the unidirectionally-energized brushless DC motor including the AC voltage output winding according to one of claims 1 to 5 and the feeding mechanism, so that the unidirectionally-energized brushless DC motor including the AC voltage output winding can be operated to act as not only the motor but also the power generator.

The feeding mechanism temporarily rotates the disk in the reverse direction in starting up the unidirectionally-energized brushless DC motor including the AC voltage output winding, and the feeding mechanism supplies the electric power of the DC power supply to the first winding such that the permanent magnet located in the reverse rotation region where the torque is generated in the reverse direction is moved to the normal rotation region where the torque is generated in the normal direction and such that the disk is turned to the normal rotation while the permanent magnet does not reach the reverse rotation region in the reverse rotation direction. Accordingly, even if the permanent magnet is located in the reverse rotation region during the non-power feeding, the disk can normally be rotated, that is, the unidirectionally-energized brushless DC motor including the AC voltage output winding can normally be rotated.

A unidirectionally-energized brushless DC motor including the AC voltage output winding further includes: a position detecting disk that is rotated in coaxial with the disk, a marker for determining a feeding region or a non-feeding region being disposed according to a rotation angle of the permanent magnet on the disk in the position detecting disk; and a sensor that detects the marker disposed in the position detecting disk, and the feeding mechanism includes a switch that switches whether the power feeding is performed to the first winding according to the marker detection result of the sensor. Accordingly, the motor system can be implemented by the simple method.

EXPLANATION OF SYMBOLS 1 unidirectionally-energized brushless DC motor including AC voltage output winding
2 rotating body
3 frame
6 permanent magnet
8 position detecting disk
9 position detecting sensor
11 circuit
70(A) first magnetic core
70(B) second magnetic core
71(A) winding (first winding)
71(B) winding (second winding)

DETAILED DESCRIPTION

Figure 1:
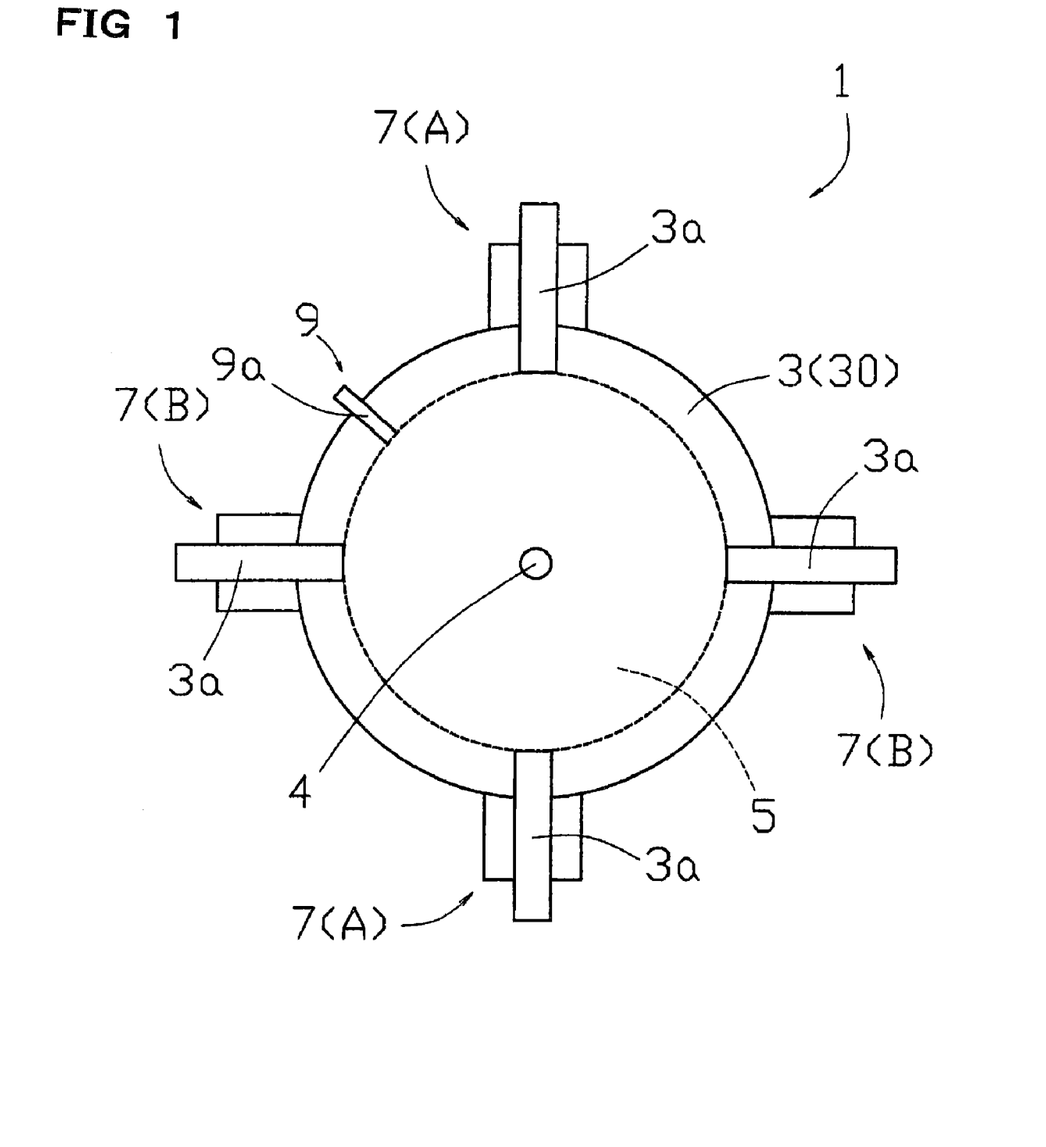
FIG. 1 is a front view illustrating an appearance of a brushless DC motor 1 according to the present invention.
Figure 2:
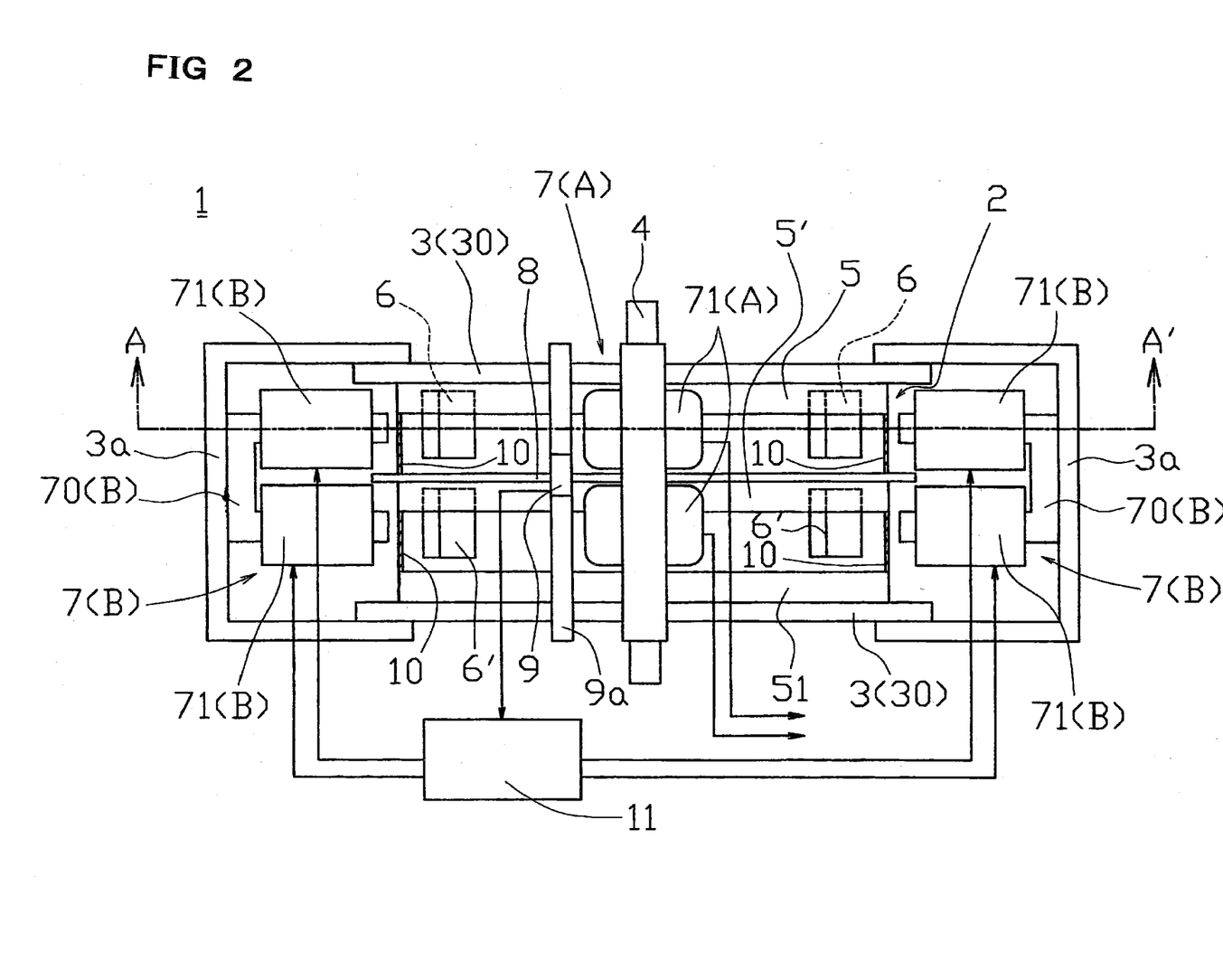
FIG. 2 is a side view illustrating an appearance of the brushless DC motor 1.
Figure 3:
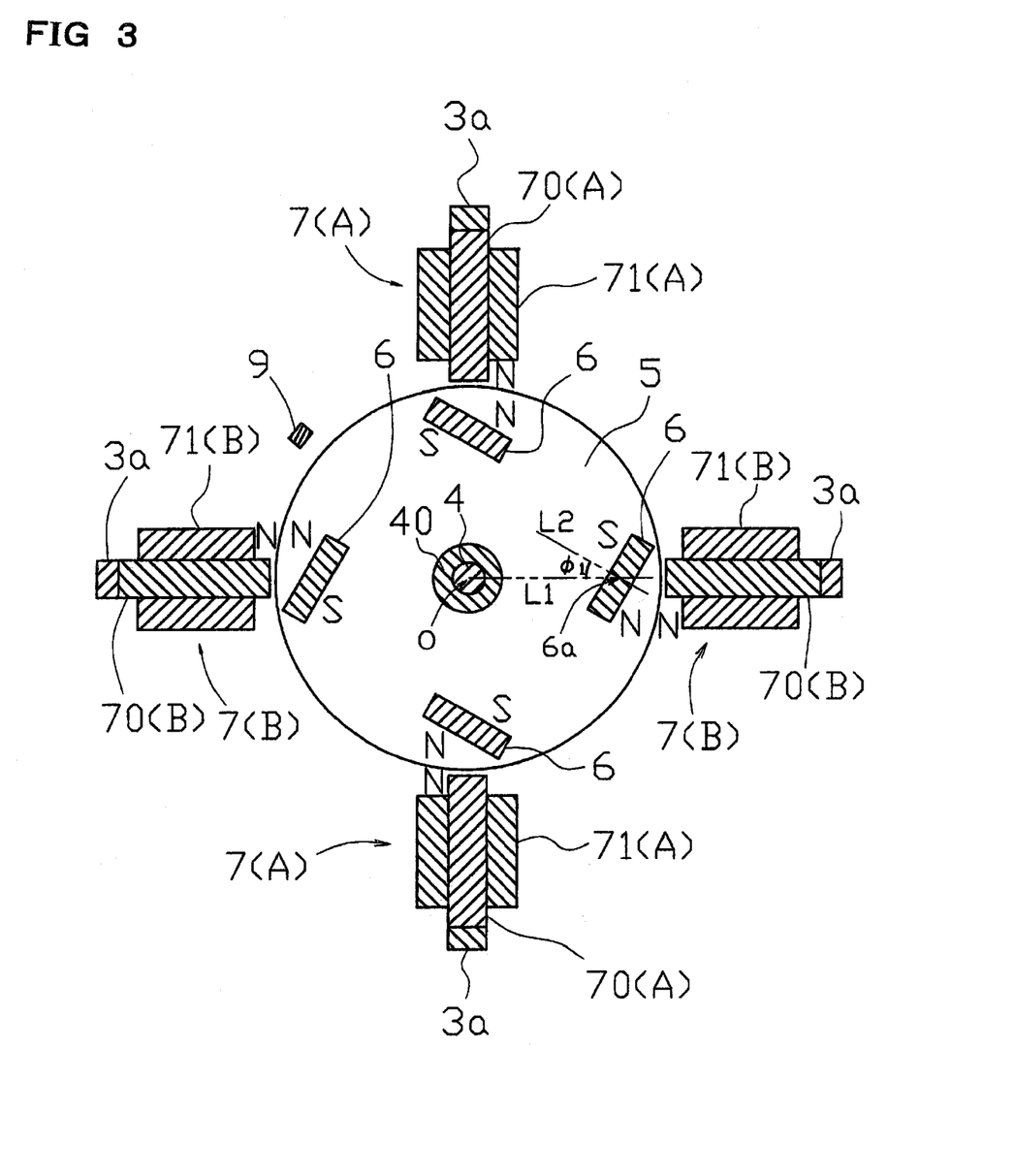
FIG. 3 is an explanatory view illustrating a sectional state taken on a line A-A' of the brushless DC motor of FIG. 2.

A unidirectionally-energized brushless DC motor 1 (hereinafter referred to as "brushless DC motor") including an AC voltage output winding according to the present invention will be described below with reference to the drawings. As illustrated in FIGS. 1 to 3, the brushless DC motor 1 of the present invention includes a rotating body 2 and a frame 3 that supports the rotating body 2. The rotating body 2 has a structure in which two disks 5 and 5', one disk 51, and one position detecting disk 8 are fixed at predetermined intervals to a shaft 4 that constitutes a rotation axis while a spacer 40 is interposed therebetween. In one of surfaces of each of the disks 5 and 5', four permanent magnets 6 and 6' are provided at equal intervals in a periphery of the disks 5 and 5'. On the other hand, in the frame 3, four electromagnets 7 are fixed by a support member 3a according to four sets of permanent magnets 6 in which one set includes two permanent magnets 6. Although described later, one of magnetic poles of a electromagnet 7 corresponds to the permanent magnet 6 (one of the two sets of permanent magnets 6 in which one set includes two permanent magnets 6) of the disk 5, and the other magnetic pole of the electromagnet 7 corresponds to the permanent magnet 6' (the other set of permanent magnets 6 in which one set includes two permanent magnets 6) of the disks 5'.

In the four electromagnets 7, a set of electromagnets 7(A) that are located opposite each other in a radial direction of the rotating body 2 is used as the motor that rotates the rotating body 2, and the remaining set of electromagnets 7(B) is used to generate the electric power. Although the electromagnet 7(B) does not act as the electromagnet, the electromagnet 7(B) is called "electromagnet" because the electromagnet 7(B) has the same configuration as the electromagnet 7(A) for the motor.

The permanent magnet 6 is formed into a plate shape in which the magnetic poles are formed in a surface and a back side, and specifically the permanent magnet 6 is a rare-earth magnet such as a neodymium magnet. The use of the permanent magnet 6 in which an N pole and an S pole are formed in the surface and the back side extends each magnetic pole plane, which allows enhancement of a rotating torque of the rotating body 2 that is of the motor.

As illustrated in FIG. 2, the permanent magnet 6 is embedded in the disk 5 to several millimeters. There is no particular limitation to a method for fixing the permanent magnet 6 to the disk 5, but the permanent magnet 6 may appropriately be fixed to the disk 5 by mounting hardware.

As illustrated in FIG. 3, the permanent magnets 6 and 6' are fixed such that an angle $\phi_1$ at which a straight line L1 passing through a center O of the disks 5 and 5' (rotating body 2) and a center 6a of the permanent magnets 6 and 6' and a straight line L2 in a magnetic pole direction of the permanent magnets 6 and 6', that is, normal to the surface or back side of the permanent magnets 6 and 6' intersect each other is set to a range of $0° < \phi_1 \leq 60°$ when viewed from the center O of the disks 5 and 5'. In the permanent magnets 6 and 6', a polarity of the magnetic pole plane in an outside direction of the disks 5 and 5' is identical to a polarity of the magnetic pole that is opposite the permanent magnets 6 and 6' of the electromagnet 7(A).

The polarity of the magnetic pole plane in the outside direction (or inside direction) of each of the four permanent magnets 6 provided in the disk 5 and the polarity of the magnetic pole plane in the outside direction (or inside direction) of each of the four permanent magnets 6' provided in the disk 5' are inverted. Specifically, the magnetic pole plane of the N pole is orientated toward the outside of the disk 5 in the permanent magnet 6 provided in the disk 5, and the magnetic pole plane of the S pole is orientated toward the outside of the disk 5 in the permanent magnet 6' provided in the disk 5'. This is because the polarities of the two magnetic poles of the electromagnet 7(A) are different from each other. One of the magnetic poles of the electromagnet 7(A) is opposite the magnetic pole plane outside the permanent magnet 6 of the disk 5, and the other magnetic pole of the electromagnet 7(A) is opposite the magnetic pole plane outside the permanent magnet 6' of the disk 5'. Accordingly, the polarity of the magnetic pole plane of the permanent magnet 6 of the disk 5 that is opposite to one of the magnetic poles of the electromagnet 7(A) is different from the polarity of the magnetic pole plane of the permanent magnet 6' of the disk 5' that is opposite to the other magnetic pole of the electromagnet 7(A). The two disks 5 and 5' are overlapped and fixed by the spacer 40 such that positions in a circumferential direction of the permanent magnets 6 and 6' included in the disks 5 and 5' become identical to each other. Accordingly, the brushless DC motor 1 wholly includes the four sets of permanent magnets 6 and 6' in which one set includes two permanent magnets, that is, a total of eight permanent magnets 6 and 6'. On the other hand, the brushless DC motor 1 wholly includes the four electromagnets 7, that is, the two electromagnets 7(A) for the motor and the two electromagnets 7(B) for the power generator.

As described above, the one disk 5, the one disk 5', and the one disk 51 are fixed in this order in the axial direction of the brushless DC motor 1 by the spacer 40. The position detecting disk 8 is fixed to the central disk 5' so as to be coaxial with the disk 5'. The position detecting disk 8 is used to detect rotational positions (rotation angles) of the permanent magnets 6 and 6'. The position detecting disk 8 has a diameter that is slightly larger than those of the disks 5 and 5' and a disk 51, and the position detecting disk 8 is made of a transparent synthetic resin. A predetermined region of the large diameter portion projected from the peripheral edge of the disk 5(A) of the position detecting disk 8 includes a marker that is blackened to specify the rotational positions of the permanent magnets 6 and 6'. A position detecting sensor 9 is attached to the frame 3 by a support member 9a. The position detecting sensor 9 detects the colored region (marker) of the position detecting disk 8 to specify the rotational positions (rotation angles) of the permanent magnets 6 and 6'. Therefore, the time for the electromagnet 7(A) to be energized is determined by specifying the rotational positions (rotation angles) of the permanent magnets 6 and 6'. The frame 3, the support member 3a, the spacer 40, and the support member 9a are made of a non-metallic material such as a synthetic resin.

The centers of the disk 5, disk 5', disk 51, and position detecting disk 8 are pierced by the shaft 4, and the shaft 4, the disk 5, the disk 5', the disk 51, the permanent magnet 6, the permanent magnet 6', and the position detecting disk 8 are fixed and integrally rotated as the rotating body 2. As illustrated in FIG. 1, in a peripheral edge portion of the rotating body 2, a film 10 is bonded so as to cover the whole peripheral edge portions of the disk 5, disk 5', and disk 51. Air in the rotating body 2 is sealed by the film 10. Accordingly, when the rotating body 2 is rotated, because the inside air is rotated along with the rotating body 2, the permanent magnet 6 is not subjected to the air resistance caused by the rotation. Therefore, the air resistance of the rotating body 2 can be reduced to improve the rotation efficiency of the brushless DC motor 1. The film 10 is made of a material that has no influence on action and reaction of the electromagnetic force between the permanent magnets 6 and 6' and the electromagnets 7(A) and 7(B). For example, preferably a thin synthetic resin film is used as the film 10.

As illustrated in FIGS. 2 and 3, in the electromagnets 7(A) and 7(B), windings 71(A) and 71(B) are wound around substantial U-shape magnetic cores 70(A) and 70(B). In the electromagnet 7(A) for the motor, the magnetic poles having the different polarities are formed in both end portions of the magnetic core 70(A) by passage of current through the winding 71(A). In the electromagnet 7(B) for the power generation, a magnetic field around the winding 71(B) including the magnetic core 70(B) is changed according to the moving permanent magnets 6 and 6', whereby induced electromotive forces are generated at both ends of the winding 71(B) by electromagnetic induction. Accordingly, the winding 71(B) is the "AC voltage output winding". The windings 71(A) of the electromagnets 7(A) are collectively connected in series, in parallel, or in series-parallel, and a DC power supply supplies the electric power to two terminals of each winding 71(B). The windings 71(B) of the electromagnets 7(B) are connected in series, in parallel, or in series-parallel to form a single-phase winding or a multi-phase winding, and the single-phase winding or the multi-phase winding is connected to various DC power consumption devices such as an AC lamp and an AC motor. Alternatively, AC voltage is rectified into DC voltage, and the winding may be connected to a DC power consumption device.

As illustrated in FIGS. 2 and 3, the electromagnet 7(A) for the motor corresponds to the set of permanent magnets 6 and 6', in which one set includes the two permanent magnets and two magnetic poles are provided in two stages in the disks 5 and 5', and the electromagnet 7(A) for the motor is disposed with a predetermined gap length. As described above, the polarity of the magnetic pole of the electromagnet 7(A) for the motor and the polarity of the magnetic pole plane of the permanent magnet 6 opposite each magnetic pole of the electromagnet 7(A) are identical to each other, and the polarity of the magnetic pole plane of the permanent magnet 6 provided in the disk 5 and the polarity of the permanent magnet 6' provided in the disk 5' are inverted between the disk 5 and the disk 5'. In the brushless DC motor 1, the rotating body 2 has the two-stage configuration in which the permanent magnet 6 fixed to the disk 5 and the permanent magnet 6' fixed to the disk 5' are provided, the electromagnet 7(A) is formed into the U-shape, and the two magnetic poles correspond to the two-stage permanent magnet 6 and permanent magnet 6', respectively. Both magnetic fluxes of the permanent magnet 6 and permanent magnet 6' are utilized in order to rotate the rotating body 2, which allows improvement of electric power-mechanical power energy conversion efficiency of the brushless DC motor 1.

The electromagnet 7(A) is fixed to the frame 3 such that an angle $\phi_2$ at which a straight line (not illustrated) connecting the center O of the disks 5 and 5' (rotating body 2) and the center of the electromagnet 7(A) and a magnetic flux center axis (not illustrated) of the electromagnet 7(A) intersect each other becomes $0°<\phi_2 \leq 20°$ when viewed from the direction of the center O of the disk 5. When the angle $\phi_2$ is set to the range of $0° \leq \phi_2 \leq 20°$, the effect that a O-torque characteristic (described later) is changed is obtained compared with the case of $\phi_2=0$. FIGS. 1 to 3 illustrate the state of $\phi_2=0$.

The electromagnet 7(B) for the power generation has the same configuration as the electromagnet 7(A) for the motor, and is disposed with a predetermined gap length such that both ends of the U-shape iron core 70(B) correspond to the permanent magnets 6 and 6' provided in two stages in the disks 5 and 5'.

The frame 3 has the shaft 4 as the axis center, and the frame 3 rotatably supports the rotating body 2. The electromagnets 7(A) and 7(B) and the position detecting sensor 9 are fixed to the frame 3. As illustrated in FIG. 1, the frame 3 includes two frame plates 30 that are coupled opposite each other at a predetermined interval. Each of the two frame plates 30 has a diameter that is larger than the maximum diameter of the rotating body 2, that is, the diameter of the position detecting disk 8. Although not illustrated, a bearing is provided at a position that supports the axis of the shaft 4 of each frame plate 30.

Any sensor may be used as the position detecting sensor 9 as long as the sensor can detect the position (rotation angle) of the position detecting disk 8 that is rotated along with the disk 5. For example, a photo interrupter may be used as the position detecting sensor 9. The position detecting sensor 9 is connected to a circuit 11 that supplies the electric power from the DC power supply (not illustrated) to the winding 71(A) of the electromagnet 7(A), and the position detecting sensor 9 provides the time at which the power feeding is performed to the winding 71(A) of the electromagnet 7(A) to the circuit 11. The position detecting sensor 9 of the embodiment transmits a detection signal indicating that a transparent region (portion that is not the colored region (marker)) of the position detecting disk 8 is detected to the circuit 11 while the transparent region is detected. The circuit 11 supplies the electric power of the DC power supply to the winding 71(A) of the electromagnet 7(A) at the time the detection signal is received from the position detecting sensor 9. Specifically, for example, the circuit 11 turns on a switch (not illustrated) to perform the power feeding to the winding 71(A) of the electromagnet 7(A) while the photo interrupter that is of the position detecting sensor 9 receives an optical signal, and the circuit 11 turns off the switch to stop the power feeding while the photo interrupter does not receive the optical signal.

The colored region (marker) is provided in the ring large diameter portion of the position detecting disk 8 projected from the peripheral edge of the disk 5'. When the position detecting sensor 9 detects the colored region by adjusting the position of the colored region, a torque can be generated in the reverse rotation direction (clockwise direction in FIG. 3) of the rotating body 2 (disk 5) in performing the power feeding to the winding 71(A) of the electromagnet 7(A). The position detecting sensor 9 detects the colored region (marker) to stop the power feeding to the winding 71(A) of the electromagnet 7(A), which allows the generation of the torque in the reverse rotation direction of the rotating body 2. Although the circuit 11 is not described in detail, a type of circuit in which energy of the winding 71(A) of the electromagnet 7(A) is not consumed by resistance, but the energy is regenerated to the power supply is preferably used as the circuit 11. For example, a circuit in which only two self arc-suppressing elements usually used in an SRM (Switched Reluctance Motor) may be used as the circuit 11.

Figure 4:
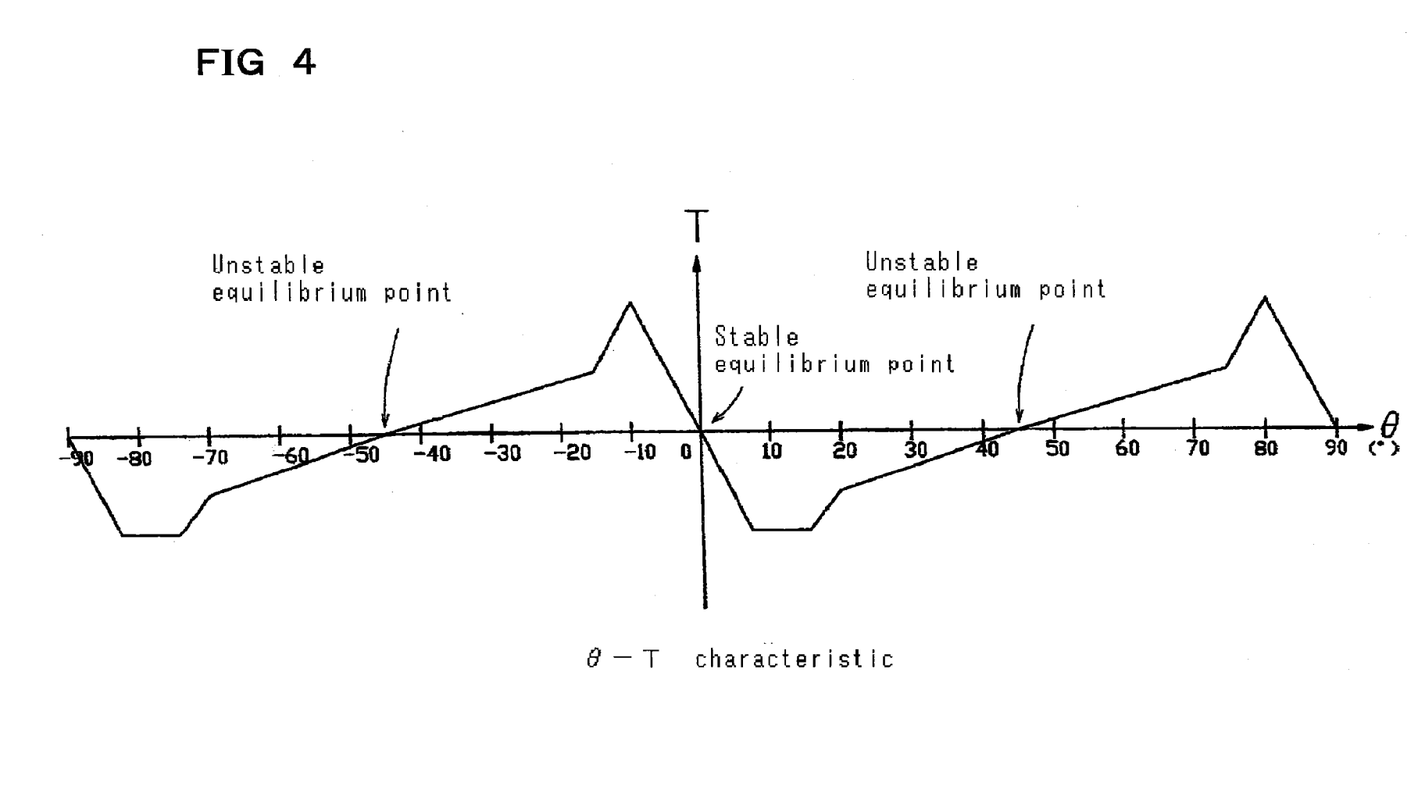
FIG. 4 is an explanatory view illustrating a θ-T characteristic when electric power is not supplied to an electromagnet 7(A).

As described above (see FIG. 3), in the permanent magnets 6 and 6', the angle $\phi_1$ at which the straight line L1 passing through the center O of the disks 5 and 5' (rotating body 2) and the center 6a of the permanent magnets 6 and 6' and the straight line L2 in the magnetic pole direction of the permanent magnets 6 and 6', that is, normal to the surface or back side of the permanent magnets 6 and 6' intersect each other is set to the range of $0°<\phi_1 \leq 60°$ when viewed from the center O of the disks 5 and 5'. When a gradient of the permanent magnets 6 and 6' is set as described above, a θ-T characteristic of FIG. 4 is obtained. At this point, θ is a mechanical angle from the center of the electromagnet 7(A) to the center of the permanent magnets 6 and 6 when measured in the normal rotation direction (counterclockwise direction in FIG. 3) of the rotating body 2 (disks 5 and 5'), and T is a detent torque (cogging torque) that is of a torque generated in the normal rotation direction by an attractive force between the magnetic core 70(A) and the permanent magnets 6 and 6' when the power feeding is not performed to the winding 71(A) of the electromagnet 7(A). As can be seen from FIG. 4, the detent torque becomes zero in the state of θ=0°, that is, in the state in which the center of the permanent magnet 6 is located at the front of the center of the electromagnet 7(A), and the state of θ=0° is a stable equilibrium point at which the disk 5 is stopped.

Figure 5:
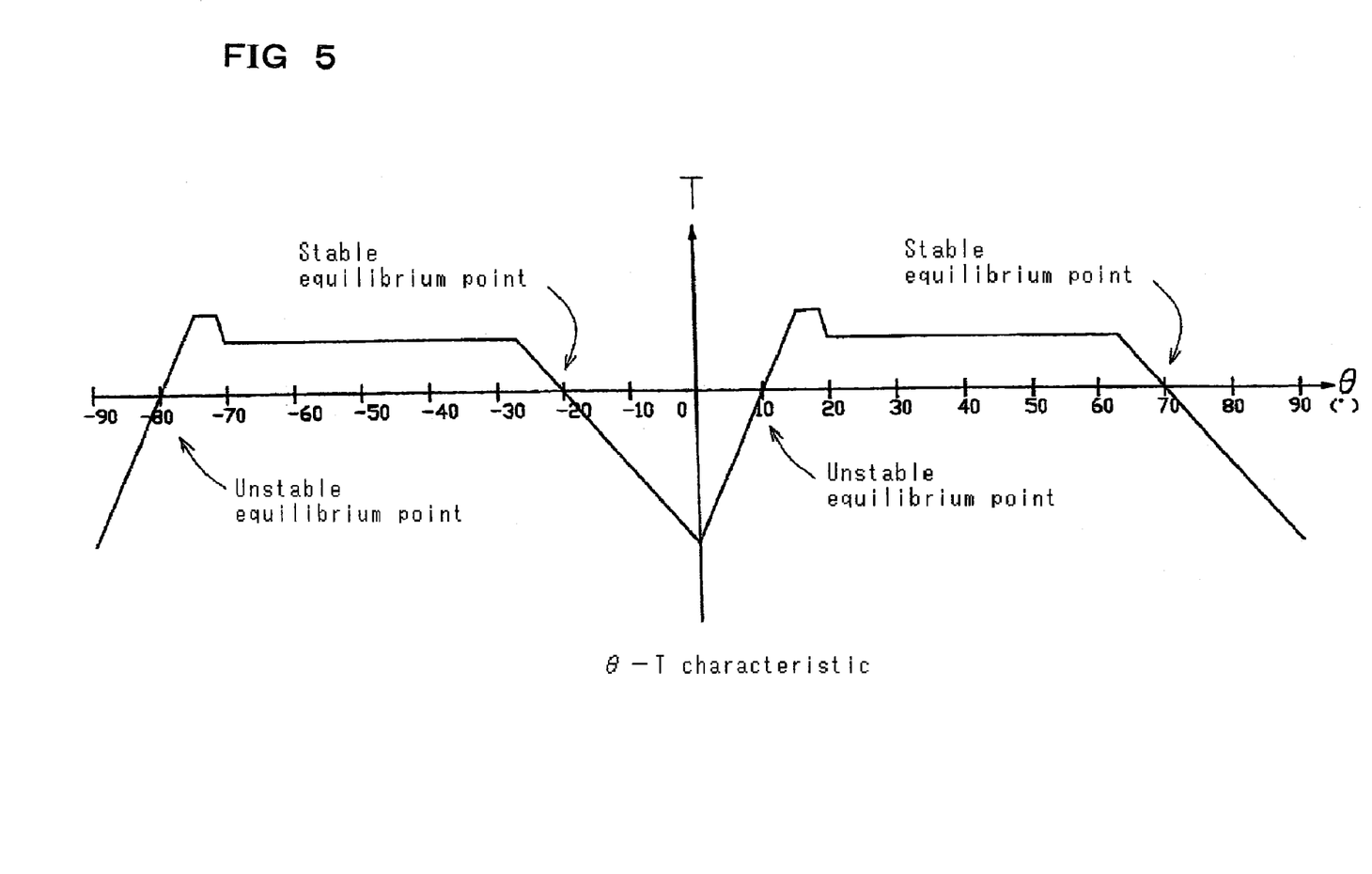
FIG. 5 is an explanatory view illustrating a θ-T characteristic when constant DC current is supplied to the electromagnet 7(A).

On the other hand, assuming that T is an electromagnetic torque in the normal rotation direction of the disk 5, which is generated between the electromagnet 7(A) and permanent magnet 6 when DC current of, for example, 1.90 A is supplied to the winding 71(A) of the electromagnet 7(A) with the DC power supply, a θ-T characteristic of FIG. 5 is obtained. When the current supplied to the electromagnet 7(A) is varied, the stable equilibrium point and the unstable equilibrium point are changed. The stable equilibrium point and the unstable equilibrium point mean one position (point) in which the permanent magnets 6 and 6' are located in the stable equilibrium state with respect to the electromagnet 7(A) and one position (point) in which the permanent magnets 6 and 6' are located in the unstable equilibrium state, respectively. In both the stable equilibrium state and the unstable equilibrium state, balance is established between an attractive force and a repulsive force of the electromagnet 7(A) and permanent magnet 6. In the stable equilibrium state, even if the disk 5 is rotated in any direction, a force is applied in the opposite direction to the rotation direction by magnetic forces of the electromagnet 7(A) and permanent magnet 6, and the disk 5 returns to the stable equilibrium state. On the other hand, in the unstable equilibrium state, when the disk 5 is rotated in any direction, a force is applied in the rotation direction of the disk 5 by the magnetic forces of the electromagnet 7(A) and permanent magnet 6, and the disk 5 does not return to the unstable equilibrium state.

As can be seen from FIG. 5, the stable equilibrium points are located at θ=−20° and θ=70°, and the unstable equilibrium points are located at θ=−80° and θ=10°. The electromagnetic torque T becomes negative at an angle width of 30°, and the electromagnetic torque T becomes positive at an angle width of 60°. Since the average value of the electromagnetic torque T becomes zero, as can be seen from FIG. 5, the angle width is narrowed and an absolute value of the electromagnetic torque T is increased in a portion in which the electromagnetic torque T becomes negative. Hereinafter the electromagnetic torque T in the portion in which the electromagnetic torque T becomes negative is referred to as "large-value narrow-angle torque". On the other hand, the angle width is spread and the absolute value of the electromagnetic torque T is decreased in a portion in which the electromagnetic torque T becomes positive. Hereinafter the electromagnetic torque T in the portion in which the electromagnetic torque T becomes positive is referred to as "small-value wide-angle torque".

Figure 6:
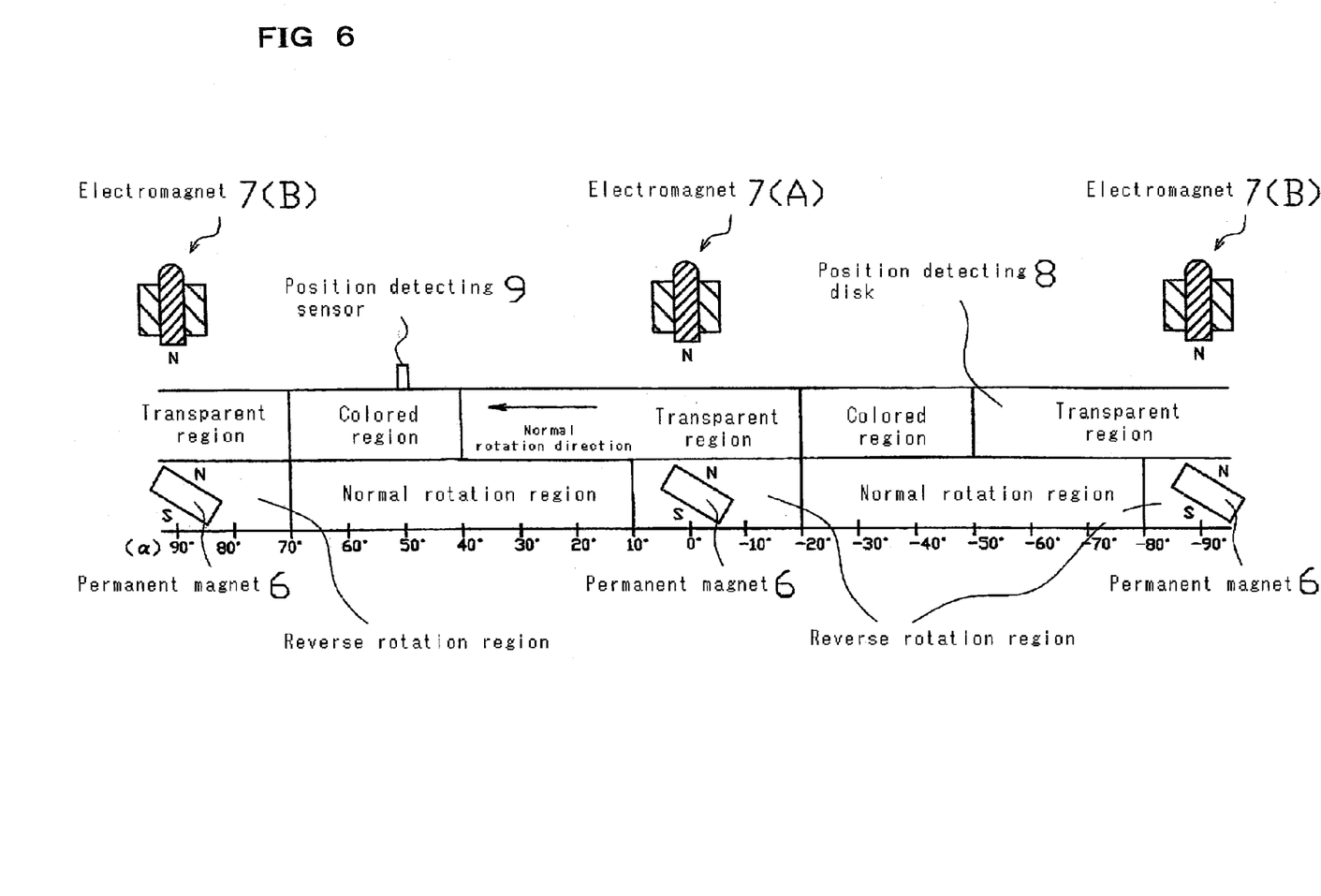
FIG. 6 is an explanatory view illustrating a positional relationship among a permanent magnet 6, electromagnets 7(A) and 7(B), a colored region and a transparent region of a position detecting disk 8, and a position detecting sensor 9 in a straight line fashion in a stable equilibrium operating state during non-power feeding to the electromagnet 7(A) when a small-value wide-angle torque is utilized.

The utilization of the small-value wide-angle torque will be discussed below. FIG. 6 is an explanatory view illustrating a positional relationship among the permanent magnet 6, the electromagnets 7(A) and 7(B), the colored region and transparent region of the position detecting disk 8, and the position detecting sensor 9 in a straight line fashion in the stable equilibrium state during non-power feeding to the electromagnet 7(A) (that is, in the state in which the detent torque becomes zero while the disks 5 and 5' are stopped). In FIG. 6, the angle α is an angle that is impressed on a stator such as the frame 3 while the front face of the electromagnet 7(A) is set to 0°, and the normal rotation of a rotor that is of the rotating body 2 (disks 5 and 5') is set to the positive orientation. The normal rotation region and the reverse rotation region are fixed with respect to the electromagnet 7(A), that is, the angle α. In the normal rotation region, the electromagnetic torque T is generated in the normal rotation direction in the disks 5 and 5' when the permanent magnets 6 and 6' are moved and located in the normal rotation region according to the rotation of the disks 5 and 5'. That is, the normal rotation region of FIG. 6 corresponds to the θ angle range where "small-value wide-angle torque" is generated in FIG. 5. In the reverse rotation region, the electromagnetic torque T is generated in the reverse rotation direction in the disks 5 and 5' when the permanent magnets 6 and 6' are moved and located in the reverse rotation region according to the rotation of the disks 5 and 5'. That is, the reverse rotation region of FIG. 6 corresponds to the θ angle range where "large-value narrow-angle torque" is generated in FIG. 5. The left direction of FIG. 6 is the normal rotation direction of the disk 5, and the colored region and transparent region of the position detecting disk 8 are moved leftward when the permanent magnet 6 is moved leftward. Both the angle width of the normal rotation region and the angle width of the transparent region are set to 60°, and both the angle width of the reverse rotation region and the angle width of the colored region are set to 30°. The normal rotation region and reverse rotation region and the transparent region and colored region are continued, the normal rotation regions and the transparent regions exist at intervals of 30°, and the reverse rotation regions and colored regions exist at intervals of 60°. The position detecting disk 8 and the position detecting sensor 9 are set such that the position detecting sensor 9 is located in the colored region when the permanent magnets 6 and 6' are located in the reverse rotation region, and such that the position detecting sensor 9 is located in the transparent region when permanent magnets 6 and 6' are located in the normal rotation region. In an example of FIG. 6, the position detecting sensor 9 is located at α=50°.

As can be seen from FIG. 6, in the stable equilibrium state in which the power feeding is not performed to the electromagnet 7(A), the permanent magnet 6 is located in the reverse rotation region, and the position detecting sensor 9 of the position detecting disk 8 performs sensing in the colored region. Because the position detecting sensor 9 transmits the detection signal to the circuit 11, the circuit 11 does not supply the electric power from the power supply to the electromagnet 7(A). Therefore, a certain type of idea is required in order that the disk 5 is rotated to start up the brushless DC motor 1 from the stable equilibrium state in which the power feeding is not performed to the electromagnet 7(A). The idea for starting up the brushless DC motor 1 is roughly classified into a first method for moving the stable equilibrium point during the non-power feeding to the normal rotation region and a second method for temporarily and forcedly moving the permanent magnet 6 to the normal rotation region in the start-up.

In the first method for moving the stable equilibrium point during the non-power feeding to the normal rotation region, the electromagnet 7(B) is located with respect to the permanent magnets 6 and 6' such that the positional relationship between the electromagnet 7(A) and the permanent magnet 6 in stopping the disks 5 and 5' in the stable equilibrium state having the detent torque of zero because of no supply of the electric power to the winding 71(A) of the electromagnet 7(A) becomes a relationship in which the torque in the normal direction of the disks 5 and 5' is continuously generated only at a predetermined rotation angle of the disks 5 and 5' in starting the supply of the electric power to the winding 71(A) of the electromagnet 7(A). That is, the detent torque (θ-T characteristic) is changed by moving the electromagnet 7(B) from the current position, that is, the position in which the electromagnet 7(B) is separated from the electromagnet 7(A) by 90°, whereby the permanent magnets 6 and 6' are located in the normal rotation region in the stable equilibrium state. When the permanent magnets 6 and 6' are located in the normal rotation region, because the sensing position of the position detecting sensor 9 exists in the transparent region, the power feeding is started to start up the disks 5 and 5', that is, the brushless DC motor 1, which allows the brushless DC motor 1 to be normally rotated.

For example, the detent torque (θ-T characteristic) is changed such that the permanent magnet 6 near the electromagnet 7(A) is located at α=11° in the stable equilibrium state. At this point, as can be seen from FIG. 6, the permanent magnets 6 and 6' are included in the normal rotation region, and the sensing position of the position detecting sensor 9 is included in the transparent region. The normal rotation region exists over the range of 70°-11°=59° in the normal rotation direction of the disk 5, and the transparent region also exists over the range of 59°. Accordingly, while the disks 5 and 5' are rotated by 59°, the power feeding is performed to the electromagnet 7(A), and the disks 5 and 5' are normally rotated. When the rotation angle of the disks 5 and 5' reaches 60° to become α=71°, the permanent magnets 6 and 6' are included in the reverse rotation region. However, because the sensing position of the position detecting sensor 9 is also included in the colored region, the power feeding to the electromagnet 7(A) is stopped. Therefore, the electromagnetic torque T generated by the electromagnet 7(A) becomes zero, and the detent torque T emerges. The detent torque T substantially has a positive value in the reverse rotation region, and inertia moment exists in the disks 5 and 5', thereby continuing the normal rotation of the disks 5 and 5'. When the permanent magnets 6 and 6' pass by the reverse rotation region having the angle width of 30°, the permanent magnets 6 and 6' enter the normal rotation region having the angle width of 60° again, thereby continuing the normal rotation of the disks 5 and 5'. In order that the permanent magnets 6 and 6' near the electromagnet 7(A) are located at α=11° in the stable equilibrium state of the detent torque T in which the power feeding is not performed to the electromagnet 7(A), it is necessary that the two electromagnets 7(B) be moved in the normal rotation direction of the disks 5 and 5' by 22°. Hence, it is necessary that the electromagnet 7(B) be moved from the position at α=90° to the position at α=112°. However, α=112° becomes the proper position when the two electromagnets 7(A) and the two electromagnets 7(B) are provided.

On the other hand, the second method for temporarily and forcedly moving the permanent magnet 6 to the normal rotation region in the start-up includes a method (2-1) for temporarily performing the power feeding to the electromagnet 7(A) irrespective of the detection of the colored region with the position detecting sensor 9 and a method (2-2) for providing the narrow transparent region in the colored region.

The method (2-1) for temporarily performing the power feeding to the electromagnet 7(A) irrespective of the detection of the colored region with the position detecting sensor 9, for example, is realized by adding a circuit 11a (not illustrated) to the circuit 11 that supplies the electric power of the DC power supply to the electromagnet 7(A). The circuit 11a supplies the electric power of the DC power supply to the electromagnet 7(A) only for a predetermined period when a push button B (not illustrated) is pushed. More specifically, in the start-up of the brushless DC motor 1, power feeding is performed to the electromagnet 7(A) by pushing the push button B, the disks 5 and 5' (permanent magnets 6 and 6') that are stopped in the stable equilibrium state of FIG. 6 is temporarily rotated in the reverse direction, the permanent magnets 6 and 6' located in the reverse rotation region are moved to the normal rotation region, and the disks 5 and 5' are turned to the normal rotation in the normal rotation region while the permanent magnets 6 and 6' do not directly reach the reverse rotation region in the reverse rotation direction. That is, when the push button B is pushed, the disks 5 and 5' are reversely rotated, the permanent magnets 6 and 6' reach the normal rotation region, and the power feeding is performed to the electromagnet 7(A) for a period (rotation angle) necessary for the disks 5 and 5' to be turned to the normal rotation while the permanent magnets 6 and 6' exist in the normal rotation region.

Figure 7:
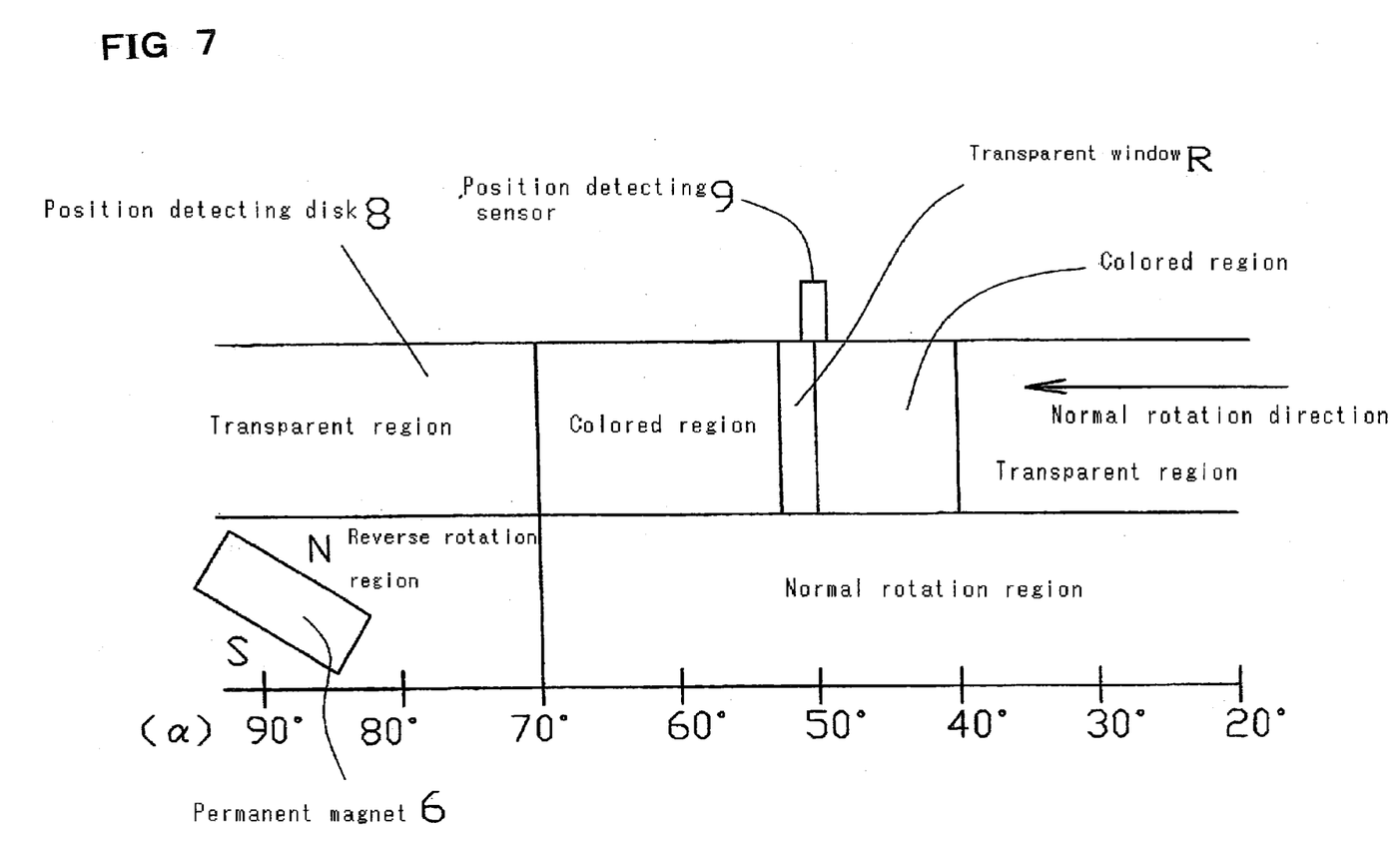
FIG. 7 is an explanatory view of a transparent window region R provided in the colored region.

In the method (2-2) for providing the narrow transparent region in the colored region, the transparent region having a predetermined width is provided in the position detecting disk 8 in the sensing position of the position detecting sensor 9 in the state in which the disk 5 is stopped in the stable equilibrium state having the detent torque T while the electric power is not supplied to the winding 71(A) of the electromagnet 7(A). That is, as illustrated in FIG. 7, a transparent window region R having a predetermined angle width is provided in the colored region having the angle width of 30°. The transparent window region R has the width from the central sensing position of the position detecting sensor 9 in the normal rotation direction of the disk 5' (position detecting disk 8). Because the transparent window region R is located in the sensing position of the position detecting sensor 9, when the circuit 11 is operated, the power feeding is immediately performed to the winding 71(A) of the electromagnet 7(A) for a certain period (rotation angle). The disks 5 and 5' (permanent magnets 6 and 6') are rotated in the reverse direction by performing the power feeding to the electromagnet 7(A) as described above, the permanent magnets 6 and 6' located in the reverse rotation region are moved to the normal rotation region, and the disk 5 is turned to the normal rotation in the normal rotation region while the permanent magnets 6 and 6' do not reach the reverse rotation region in the reverse rotation direction. Therefore, the transparent window region R has the angle width in which the power feeding is performed to the electromagnet 7(A) for the necessary period. During the necessary period, the disks 5 and 5' are reversely rotated, the permanent magnets 6 and 6' reach the normal rotation region, and the disks 5 and 5' are turned to the normal rotation while the permanent magnets 6 and 6' exists in the normal rotation region. During usual rotation, due to a poor transient characteristic of the position detecting sensor 9, the transparent window region R is not detected and the control operation is not generated.

Figure 8:
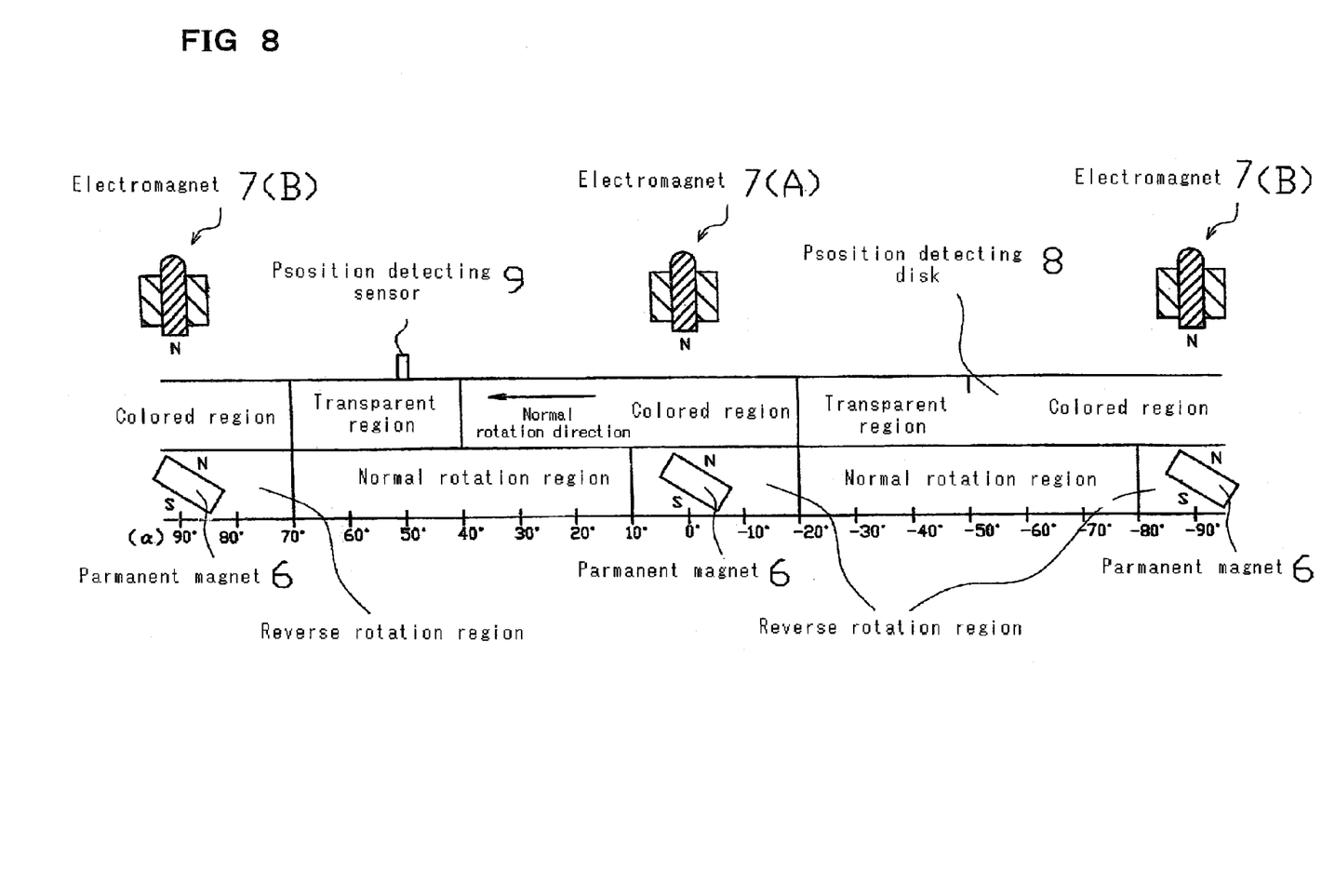
FIG. 8 is an explanatory view illustrating a positional relationship among the permanent magnet 6, the electromagnets 7(A) and 7(B), the colored region and transparent region of the position detecting disk 8, and the position detecting sensor 9 in a straight line fashion in the stable equilibrium operating state during non-power feeding to the electromagnet 7(A) when a large-value narrow-angle torque is utilized.

The utilization of the large-value narrow-angle torque will be discussed below. At this point, it is necessary that the colored region of the position detecting disk 8 be changed to the transparent region while the transparent region is changed to the colored region in FIG. 6 illustrating the settings of the position detecting disk 8 and position detecting sensor in utilizing the small-value wide-angle torque. FIG. 8 illustrates the state in which the colored region of the position detecting disk 8 is changed to the transparent region while the transparent region is changed to the colored region. FIG. 8 illustrates the stable equilibrium state (that is, the state in which the detent torque becomes zero while the disks 5 and 5' are stopped) during the non-power feeding to the electromagnet 7(A). As can be seen from FIG. 8, the permanent magnets 6 and 6' exist in the reverse rotation region, and the position detecting sensor 9 exists in the transparent region. Therefore, the position detecting sensor 9 transmits the detection signal to the circuit 11, and the circuit 11 supplies the electric power from the power supply to the electromagnet (A), thereby rotating the brushless DC motor 1 in the reverse rotation direction. No particular idea for starting up the brushless DC motor 1 is required when the large-value narrow-angle torque is utilized. However, when the electromagnet (B) is deviated from a fixed position, it is necessary to pay attention such that the permanent magnets 6 and 6' are not moved to the outside of the reverse rotation region in the stable equilibrium state during the non-power feeding.

According to the brushless DC motor 1 of the present invention as described above, the electric power can directly be generated by the rotation of the rotating body 2 (disks 5 and 5') while the brushless DC motor 1 acts as the motor by the rotation of the rotating body 2. According to the brushless DC motor 1 of the present invention, the rotation of the rotating body 2 by the electromagnet 7(A) for the motor and the power generation by the electromagnet 7(B) for the power generation are simultaneously performed, so that the motor function and the power generation function of being able to obtain the continuous electromotive force can simultaneously be exerted.

The embodiment of the present invention may appropriately be changed and practiced without departing from the scope of the technical thought of the present invention. For example, in the embodiment, the electromagnet 7(B) including the magnetic core 70(B) and the winding 71(B) is used as the means for generating the electric power. Only the winding 71(B) may be used as the means for generating the electric power. However, the electric power can efficiently be generated when the electromagnet 7(B) including the magnetic core 70(B) and the winding 71(B) is used as the means for generating the electric power, that is, when the magnetic core 70(B) is inserted in the winding 71(B).

The two electromagnets 7(A) for the motor and the two electromagnets 7(B) for the power generation are used in the embodiment. The number of electromagnets 7(A) for the motor or the number of electromagnets 7(B) for the power generation is not limited to two, but is appropriately changed. However, preferably the number of electromagnets 7(A) for the motor or the number of electromagnets 7(B) for the power generation is determined such that the electromagnetic coupling is not generated between the adjacent electromagnets 7(A) for the motor, the adjacent electromagnets 7(B) for the power generation, or the electromagnet 7(A) for the motor and the electromagnet 7(B) for the power generation.

In the configuration of the embodiment, the two sets of electromagnets 7(A) for the motor and the two sets of electromagnets 7(B) for the power generation are provided with respect to the four sets of permanent magnets 6. Alternatively, the four electromagnets 7(A) for the motor are provided with respect to the four sets of permanent magnets 6, and an arbitrary number of electromagnets 7(B) for the power generation may appropriately be provided. Alternatively, for example, the one electromagnet 7(B) and the three electromagnets 7(A) may be provided. Alternatively, the one electromagnet 7(A) and the three electromagnets 7(B) may be provided.

In the configuration of the embodiment, the two disks 5 including the permanent magnets 6 are provided. Alternatively, only one disk 5 may be provided. However, preferably the two disks 5 are provided in order to enhance the energy efficiency as the motor of the brushless DC motor 1.

In the embodiment, the power feeding is performed to the winding 71(A) of the electromagnet 7(A) at the time the electromagnetic torque T becomes the positive value in FIG. 5, that is, the time the small-value wide-angle torque is generated. However, the present invention is not limited to the embodiment, for example, the power feeding may be performed to the winding 71(A) of the electromagnet 7(A) at the time the electromagnetic torque T becomes the negative value, that is, the time the large-value narrow-angle torque is generated.

INDUSTRIAL APPLICABILITY

For example, the present invention can be applied to the unidirectionally-energized brushless DC motor including the AC voltage output winding, the brushless DC motor rotating the rotating body to act as the motor and directly generating the electric power by the rotation of the rotating body, and the motor system including the brushless DC motor.

The invention claimed is:

1. A unidirectionally-energized brushless DC motor including an AC voltage output winding, the unidirectionally-energized brushless DC motor comprising:
a frame;
a disk that is rotatably attached to the frame;
a plurality of plate-like permanent magnets that are disposed on the disk at equal intervals around the disk, magnetic poles being formed in a surface and a back side of the permanent magnet;
a predetermined number of first magnetic cores that are fixed to the frame according to the plurality of permanent magnets;
a first winding that is wound around each of the first magnetic cores, DC power being supplied to the first winding;
a predetermined number of second magnetic cores that are fixed to the frame; and
a second winding that is wound around the second magnetic core and connected to a power consumption device, wherein
the permanent magnet is located such that an angle formed by a straight line passing through a center of the disk and a center of the permanent magnet and a normal line in a center of a magnetic pole plane of the permanent magnet ranges from 0° to 60°,
whereby, when constant DC current is continuously supplied to the first winding, a large-value narrow-angle torque in which a rotation angle range where the disk is rotated in a reverse direction is narrowed while a torque value is large and a small-value wide-angle torque in which a rotation angle range where the disk is rotated in a normal direction is spread while the torque value is small are generated in a characteristic curve of a rotation angle of the permanent magnet and an electromagnetic torque, the rotation angle of the permanent magnet being measured with respect to the permanent magnet in a stable equilibrium operating state based on the first magnetic core, a detent torque becoming zero in the stable equilibrium operating state, the detent torque being generated by an attractive force between the first magnetic core and the permanent magnet during non-power feeding to the first winding, the electromagnetic torque being generated by current of the first winding and the permanent magnet, and
the power feeding is performed to the first winding only when the large-value narrow-angle torque is generated, or only when the small-value wide-angle torque is generated.

2. The unidirectionally-energized brushless DC motor including an AC voltage output winding according to claim 1, comprising the two disks that are coaxially fixed to each other,
wherein a polarity of the permanent magnet disposed in one of the disks and a polarity of the permanent magnet disposed in the other disk are different from each other, and
the first magnetic core and the second magnetic core are fixed such that one of end portions corresponds to the permanent magnet disposed in one of the disks while the other end portion corresponds to the permanent magnet disposed in the other disk.

3. The unidirectionally-energized brushless DC motor including an AC voltage output winding according to claim 1, wherein the even-numbered first magnetic cores exist, the first magnetic cores are fixed in a certain position of the disk and a position that is separated from the position by 180°, and identical current is passed through the two first windings that are wound around the first magnetic cores, the first windings being opposite each other, and
the even-numbered second magnetic cores exist, the second magnetic cores are fixed in a certain position of the disk and a position that is separated from the position by 180°, and identical current is passed through the two second windings that are wound around the second magnetic cores, the second windings being opposite each other.

4. The unidirectionally-energized brushless DC motor including an AC voltage output winding according to claim 1, wherein the frame and the disk are made of a non-metallic material.

5. The unidirectionally-energized brushless DC motor including an AC voltage output winding according to claim 1, wherein, when the disk is stopped because electric power is not supplied to the first winding, the second magnetic core is located with respect to the permanent magnet such that a positional relationship between the first winding and the permanent magnet becomes a positional relationship in which the torque in the normal direction of the disk or the torque in the reverse direction of the disk is continuously generated at a predetermined rotation angle of the disk when the supply of the electric power to the first winding is started.

6. A motor system comprising:
a unidirectionally-energized brushless DC motor including an AC voltage output winding according to claim 1; and
a feeding mechanism that supplies electric power of a DC power supply to the first winding at the time a torque is obtained in the normal direction of the unidirectionally-energized brushless DC motor including the AC voltage output winding, temporarily rotates the disk in the reverse direction in starting up the unidirectionally-energized brushless DC motor including the AC voltage output winding, and supplies the electric power of the DC power supply to the first winding such that the permanent magnet located in a reverse rotation region where the torque is generated in the reverse direction during the stopping is moved to a normal rotation region where the torque is generated in the normal direction and such that the disk is turned to the normal rotation while the permanent magnet does not reach the reverse rotation region in the reverse rotation direction.

7. The motor system according to claim 6, wherein the unidirectionally-energized brushless DC motor including the AC voltage output winding further includes:
a position detecting disk that is rotated in coaxial with the disk, a marker for determining a feeding region or a non-feeding region being disposed according to a rotation angle of the disk in the position detecting disk; and
a sensor that detects the marker disposed in the position detecting disk, and
the feeding mechanism includes a switch that switches whether power feeding is performed to the first winding according to the marker detection result of the sensor.

* * * * *